United States Patent
Mills et al.

(10) Patent No.: US 6,693,221 B1
(45) Date of Patent: Feb. 17, 2004

(54) METHOD OF PREPARING MIXTURES OF BROMOPHENOLS AND BENZOQUINONES

(75) Inventors: Ryan Christopher Mills, Clifton Park, NY (US); Timothy Leigh Chuck, Canajoharie, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/406,061

(22) Filed: Apr. 4, 2003

(51) Int. Cl.$^7$ ............................................. C07C 39/24
(52) U.S. Cl. ..................... 568/779; 552/293; 552/309; 552/310
(58) Field of Search .................. 568/779; 552/293, 552/309, 310

(56) References Cited

U.S. PATENT DOCUMENTS

| | | |
|---|---|---|
| 1,934,656 A | 11/1933 | Britton et al. |
| 3,213,114 A | 10/1965 | Braxton et al. |
| 3,306,874 A | 2/1967 | Hay |
| 3,658,852 A | 4/1972 | Schuster et al. |
| 3,794,668 A | 2/1974 | Larkins, Jr. |
| 3,796,732 A * | 3/1974 | Brenner |
| 3,859,317 A | 1/1975 | Hutchings |
| 3,870,731 A | 3/1975 | Hutchings |
| 3,933,681 A | 1/1976 | Hutchings et al. |
| 3,987,068 A | 10/1976 | Reilly |
| 4,208,339 A | 6/1980 | Costantini et al. |
| 4,482,756 A | 11/1984 | Hsu et al. |
| 4,519,948 A | 5/1985 | Hsu et al. |
| 4,522,757 A | 6/1985 | Hsu et al. |
| 5,177,258 A | 1/1993 | Becker et al. |
| 5,932,753 A * | 8/1999 | Onodera |
| 6,410,798 B2 * | 6/2002 | Maassen |

FOREIGN PATENT DOCUMENTS

EP    93540 A2    4/1983

OTHER PUBLICATIONS

Copending U.S. patent application Ser. No. 10/342,475, filed Jan. 16, 2003, by G. Soloveichik et al, entitled "Bromination of Hydroxyaromatic Compounds and Further Conversion to Dihydroxyaromatic Compounds".

Polymers of Carbonic Acid. 3. Thermotropic Polycarbonates Derived from 4,4'–Dihydroxybiphenyl and Various Diphenols. Kricheldorf and Lubbers. Macromolecules 1990, 2656–2662.

* cited by examiner

*Primary Examiner*—Michael L. Shippen
(74) *Attorney, Agent, or Firm*—Andrew J. Caruso; Patrick K. Patnode

(57) ABSTRACT

A method is described for the simultaneous preparation of 4-bromophenols and p-benzoquinones, intermediates useful in the preparation of hydroquinones and 4,4'-dihydroxybiphenyls respectively. Hydroquinones and 4,4'-dihydroxybiphenyls are useful monomers for the preparation of a variety of polymers. In one example phenol is reacted with in the presence of HBr, a catalytic amount of cupric bromide and a stoichiometric excess of oxygen under relatively mild conditions to provide a mixture of the phenol, 4-bromophenol, and 1,4-benzoquinone. Phenol conversion was 54 percent and selectivities for bromophenol and benzoquinone were 23% and 37% respectively. Limiting the amount of HBr present in the reaction mixture was shown to control the amount of benzoquinone produced.

22 Claims, No Drawings

METHOD OF PREPARING MIXTURES OF BROMOPHENOLS AND BENZOQUINONES

BACKGROUND OF THE INVENTION

This invention relates to a method of preparing in a single step, a mixture comprising a p-brominated phenol and a p-benzoquinone. More particularly the method relates to a method of preparing in a single step, a mixture of p-bromophenol and p-benzoquinone intermediates which may be separated and subsequently converted in single step transformations to dihydroxy aromatic compounds useful in the preparation of polycarbonate copolymers.

A variety of copolymers possessing useful and desirable properties comprise structural units derived from both hydroquinones and 4,4'dihydroxybiphenyls. Examples of include the polyether sulfone (CAS No. 90337-94-3) prepared from hydroquinone (HQ), 4,4'-dihydroxybiphenol (BP) and bis(4-chlorophenyl)sulfone; and the polyester (CAS No. 96892-06-7) derived from HQ, BP and a mixture of iso- and terephthalic acid. Additionally, polycarbonates comprising structural units derived from HQ, BP and another bisphenol comonomer (e.g. CAS No. 491588-47-7) show promise in a variety of materials applications.

Typically, the hydroquinone derivative and the 4,4'-dihydroxybiphenyl derivative used in the preparation of such polymers are prepared in independent manufacturing steps. Hydroquinone is typically prepared by air oxidation and fragmentation of 1,4-diisopropylbenzene, or by direct oxidation of phenol. Typically, 4,4'-dihydroxybiphenyl is obtained by oxidative coupling of 2,6-di-tert-butylphenol followed by acid mediated removal of the tert-butyl groups in the coupled product. Hydroquinones may be prepared as well by hydrolysis of a p-bromophenol as illustrated in U.S. Pat. No. 1,934,656. In addition, 4,4'-dihydroxybiphenyls may be prepared by reductive coupling of a p-bromophenol to the corresponding 4,4'-dihydroxybiphenyl as described in U.S. Pat. No. 5,177,258. Co-pending U.S. application Ser. No. 10/342,475 (filed Jan. 16, 2003) discloses an efficient means of preparing a p-bromophenol as a single intermediate which can be transformed by hydrolysis or reductive coupling into either a hydroquinone or a 4,4'-dihydroxybiphenyl. While this approach provides additional efficiencies based upon its use of a single intermediate p-bromophenol relative to known methods, improved methods continue to be sought, especially in light of the challenges presented by the rigorous conditions required for the hydrolytic transformation of the intermediate p-bromophenol to the corresponding hydroquinone.

The present invention is related to that described in co-pending U.S. application Ser. No. 10/342,475 (filed Jan. 16, 2003), but provides an alternate approach to the preparation of hydroquinones and 4,4'-dihydroxybiphenyls which eliminates the need for hydrolytic conversion of a p-bromophenol intermediate into the corresponding hydroquinone.

BRIEF SUMMARY OF THE INVENTION

In one aspect, the present invention provides a method preparing a mixture of a p-bromophenol and a p-benzoquinone, said method comprising contacting in a reaction mixture a hydroxyaromatic compound with:
(a) hydrogen bromide;
(b) at least one source of copper selected from the group consisting of copper compounds, and elemental copper; and
(c) oxygen gas;

said hydrogen bromide being present in an amount corresponding to between about 0.01 and about 0.2 moles of hydrogen bromide per mole of said hydroxyaromatic compound, said contacting taking place at a temperature in a range between about 20° C. and about 250° C.

In another aspect, the present invention relates to a method for the preparation of hydroquinones and 4,4'-dihydroxybiphenyls, said method comprising conversion of a mixture of a p-bromophenol and a p-benzoquinone into purified forms of the corresponding 4,4'-dihydroxybiphenyl derivative and the corresponding hydroquinone derivative.

DETAILED DESCRIPTION OF THE INVENTION

The present invention may be understood more readily by reference to the following detailed description of preferred embodiments of the invention and the examples included herein. In this specification and in the claims which follow, reference will be made to a number of terms which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein the term "polycarbonate" refers to polycarbonates incorporating structural units derived from one or more dihydroxy aromatic compounds and includes copolycarbonates and polyester carbonates.

As used herein, the term "melt polycarbonate" refers to a polycarbonate made by the transesterification of at least one diaryl carbonate with at least one dihydroxy aromatic compound.

"BPA" is herein defined as bisphenol A and is also known as 2,2-bis(4-hydroxyphenyl)propane, 4,4'-isopropylidenediphenol and p,p-BPA.

As used herein the term "aromatic radical" refers to a radical having a valence of at least one and comprising at least one aromatic ring. Examples of aromatic radicals include phenyl, pyridyl, furanyl, thienyl, naphthyl, phenylene, and biphenyl. The term includes groups containing both aromatic and aliphatic components, for example a benzyl group, a phenethyl group or a naphthylmethyl group. The term also includes groups comprising both aromatic and cycloaliphatic groups for example 4-cyclopropylphenyl and 1,2,3,4-tetrahydronaphthalen-1-yl.

As used herein the term "aliphatic radical" refers to a radical having a valence of at least one and consisting of a linear or branched array of atoms which is not cyclic. The array may include heteroatoms such as nitrogen, sulfur and oxygen or may be composed exclusively of carbon and hydrogen. Examples of aliphatic radicals include methyl, methylene, ethyl, ethylene, hexyl, hexamethylene and the like.

As used herein the term "cycloaliphatic radical" refers to a radical having a valance of at least one and comprising an array of atoms which is cyclic but which is not aromatic, and which does not further comprise an aromatic ring. The array may include heteroatoms such as nitrogen, sulfur and oxygen or may be composed exclusively of carbon and hydrogen. Examples of cycloaliphatic radicals include cyclopropyl, cyclopentyl cyclohexyl, 2-cyclohexylethy-1-yl, tetrahydrofuranyl and the like.

The present invention relates to a method transforming a phenol I into a mixture of a p-bromophenol II and a p-benzoquinone III

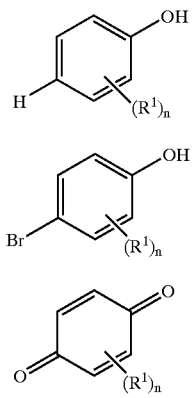

wherein, in each of structures I, II and III, $R^1$ is independently at each occurrence a halogen, $C_1$–$C_{20}$ alkyl group, $C_4$–$C_{20}$ cycloalkyl group, or a $C_4$–$C_{20}$ aryl group, and n is an integer from 0 to 4.

In one embodiment of the present invention a product mixture comprising p-bromophenol II and benzoquinone III is subjected to a separation step to provide p-bromophenol II and p-benzoquinone III in purified form. A significant advantage of the method of the present invention over known methods is that it provides the intermediate p-benzoquinone III which may be transformed under very mildly reducing conditions to hydroquinone derivative IV

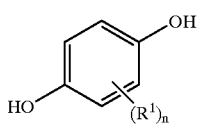

wherein $R^1$ and n are defined as in structures I–III. Purified p-bromophenol II may be transformed via reductive coupling into 4,4'-dihydroxybiphenyl derivative V

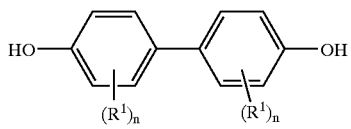

wherein $R^1$ and n are defined as in structures I–III.

In one embodiment of the mixture comprising p-bromophenol II and p-benzoquinone III is subjected to mild reduction of the p-benzoquinone component to hydroquinone IV prior to separation from p-bromophenol II. Reduction methods for transforming benzoquinones into the corresponding hydroquinones are well known in the art and include catalytic reduction using hydrogen and a noble metal catalyst, for example reduction with hydrogen gas using palladium on charcoal as the catalyst at ambient temperature and pressure.

Physical methods which may be used to separate a mixture comprising p-bromophenol II and p-benzoquinone III into purified forms of II and III include fractionation by vacuum distillation, steam distillation, reactive distillation, sublimation, crystallization, zone refining and like techniques, or a combination of one or more of such techniques. Typically, fractional distillation and crystallization are preferred. In one embodiment, the mixture of p-bromophenol II and p-benzoquinone III prepared by the method of the present invention is separated by fractional distillation and recrystallization into purified forms of p-bromophenol II and p-benzoquinone III having purities in excess of 90 percent, preferably in excess of 95 percent, and still more preferably in excess of 98 percent. In one embodiment a mixture comprising 4-bromophenol (CAS No. 106-41-2) and 1,4-benzoquinone (CAS No. 105-51-4) prepared from phenol using the method of the present invention, is separated by fractional distillation and recrystallization of the resultant distillation fractions to provide purified 4-bromophenol and 1,4-benzoquinone having purities in excess of 90 percent.

The method of the present invention is carried out by first contacting a hydroxy aromatic compound with hydrogen bromide (HBr), a source of copper, an organic solvent, and oxygen gas at a temperature in a range between about 20° C. and about 250° C., preferably between about 30° C. and about 150° C., and even more preferably between about 40° C. and about 100° C. The amount of hydrogen bromide plays a key role in producing high levels of benzoquinone product. The amount of hydrogen bromide should be in a range corresponding to between about 0.01 and about 0.2 moles, preferably between about 0.02 and about 0.15 moles, and still more preferably between about 0.04 and about 0.1 moles of hydrogen bromide per mole of said hydroxyaromatic compound.

Typically, the hydroxyaromatic compound is a phenol bearing no substituent in the position para to the phenolic OH group, for example structure I

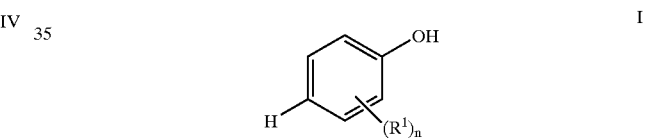

wherein $R^1$ is independently at each occurrence a halogen, $C_1$–$C_{20}$ alkyl group, $C_4$–$C_{20}$ cycloalkyl group, or a $C_4$–$C_{20}$ aryl group, and n is an integer from 0 to 4.

Examples of phenols having structure I include phenol, o-cresol, m-cresol; 2,6-xylenol; 2,5-xylenol; 2,3,5-xylenol; 2,3,6-xylenol; 2-ethylphenol, 2-propylphenol, 2-tert-butylphenol, 2-phenylphenol, and the like. Typically, phenol and o-cresol are preferred.

The method of the present invention requires only catalytic amounts of copper but typically involves the use of a substantial stoichiometric excess of oxygen. Typically, the hydroxyaromatic compound is reacted in the presence of aqueous HBr, a copper species, an organic solvent, and oxygen in a reaction vessel equipped for intimate mixing of the reactants and operation at pressures higher than atmospheric pressure. In one embodiment, the reactants other than oxygen are first charged to a batch reaction vessel and stirring is begun. Subsequently a stoichiometric excess of oxygen gas is introduced into the reaction vessel to provide a partial pressure of oxygen over the reaction mixture of from about 50 pounds per square inch (psi) to about 2000 psi, preferably from 50 psi to about 1500 psi and still more preferably from about 100 psi to about 500 psi. In an alternate embodiment, the reactants are introduced into a flow reactor, for example a continuous stirred tank reactor, agitated and exposed to oxygen under conditions corresponding to partial pressure of oxygen over the reaction mixture of from about 50 pounds per square inch (psi) to about 2000 psi, preferably from 50 psi to about 1500 psi and still more preferably from about 100 psi to about 500 psi. In almost any embodiment of the invention, the oxygen may be used advantageously in the form of pure oxygen, air, a synthetic mixture of oxygen and one or more other gases (for example a synthetic mixture of oxygen and nitrogen), or any other convenient source of oxygen which may be used as the stoichiometric oxidant. Reaction vessels for use according to the method of include stirred tank reactors, continuous stirred tank reactors and the like.

As mentioned, the source of copper employed is present in a catalytic amount and can be any copper source capable of producing copper ions under the reaction conditions. Thus, even elemental copper or a mixture of copper compounds may be used according to the method of the invention. It has been found most convenient, however, to employ a catalytic amount of copper in the form of a single soluble copper compound, such as a copper halide. The initial oxidation state of the copper compound employed does not appear to be critical, so that cuprous halides and cupric halides may be employed with reasonable interchangeability. Typically the source of copper will be selected from the group consisting of cuprous chloride, cuprous bromide, cuprous iodide, cupric chloride, cupric bromide, and cupric iodide. Owing to their greater overall stability cupric halides are typically preferred.

Typically, the source of copper employed is used in an amount sufficient to provide a concentration of copper ion in the reaction mixture in an amount corresponding to between about 0.001 and about 0.200 moles, preferably between about 0.01 and about 0.1 moles, and still more preferably between about 0.03 and about 0.07 moles of copper ion per mole of hydroxyaromatic compound.

The method of the present invention may be advantageously carried out in the presence of an organic solvent which may be a pure solvent, or a mixture of solvents. Typically it is preferred that the organic solvent comprise an organic nitrile solvent, for example acetonitrile. Organic nitrile solvents are illustrated by acetonitrile, propionitrile, butyronitrile, isopropylnitrile, benzonitrile, and mixtures thereof. In some embodiments an organic nitrile solvent is used as a mixture with one or more solvents selected from the group consisting of aliphatic ethers, aromatic ethers, aliphatic alcohols, aromatic alcohols, ketones, halogenated alkanes, halogenated aromatics, amides, aliphatic hydrocarbons, and aromatic hydrocarbons. Typically, the organic solvent is present in an amount corresponding to between about 0.01 and about 1.0 liters, preferably between about 0.01 and about 0.5 liters, and sill more preferably between about 0.1 and about 0.4 liters of organic solvent per mole of hydroxyaromatic compound employed.

When the source of hydrogen bromide is concentrated hydrobromic acid (i.e. a mixture of hydrogen bromide and water comprising about 48 percent by weight HBr and about 52 percent by weight water) it has been found beneficial in some instances to add additional water to the reaction mixture. Thus, when concentrated hydrobromic acid is employed, water is added to the reaction mixture in an amount corresponding to about 0.4 moles to about 5 moles, preferably from about 1 mole to about 5 moles, and still more preferably from about 1 mole to about 3 moles of water per mole of hydroxyaromatic compound.

In one embodiment, phenol is reacted under the conditions of the present invention to provide a mixture of 4-bromophenol with 1,4-benzoquinone. This embodiment of the present invention is practiced by contacting in a reaction mixture at a temperature in a range between about 20° C. and about 150° C., phenol with: hydrogen bromide, at least one source of copper selected from the group consisting of cupric bromide or cuprous bromide, acetonitrile; and oxygen gas. The hydrogen bromide is present in an amount corresponding to less than 0.2 moles of hydrogen bromide per mole of phenol. The source of copper is present in an amount corresponding to between about 0.01 and about 0.20 moles of copper per mole of phenol. The acetonitrile is present in an amount corresponding to from about 0.01 to about 1.0 liters of acetonitrile per mole of phenol, and the "contacting" is carried out under a partial pressure of oxygen of from about 50 to about 2000 pounds per square inch. The product obtained is a mixture comprising 4-bromophenol and 1,4-benzoquinone.

In alternate embodiment, o-cresol is reacted under the conditions of the present invention to provide a mixture of 4-bromo-2-methylphenol with methyl-1,4-benzoquinone. This embodiment of the present invention is practiced by contacting in a reaction mixture at a temperature in a range between about 20° C. and about 150° C., o-cresol with: hydrogen bromide, at least one source of copper selected from the group consisting of cupric bromide or cuprous bromide, acetonitrile; and oxygen gas. The hydrogen bromide is present in an amount corresponding to less than 0.2 moles of hydrogen bromide per mole of o-cresol. The source of copper is present in an amount corresponding to between about 0.01 and about 0.20 moles of copper per mole of o-cresol. The acetonitrile is present in an amount corresponding to from about 0.01 to about 1.0 liters of acetonitrile per mole of phenol, and the "contacting" is carried out under a partial pressure of oxygen of from about 50 to about 2000 pounds per square inch. The product obtained is a mixture comprising 4-bromo-2-methylphenol and methyl-1,4-benzoquinone.

Typically the percentage of a phenolic compound having structure I, converted to p-bromophenol II and p-benzoquinone III is at least 20 percent, preferably at least 25 percent, and still more preferably at least 30 percent. Typically, the selectivity for the production of p-bromophenol II is in a range between about 20 and about 80 percent. This means that for every mole of phenolic compound I converted to products, between about 0.2 and about 0.8 moles of a p-bromophenol II is produced. Correspondingly, the selectivity for the production of p-benzoquinone III is in a range between about 80 and about 20 percent. Other products, for example 2-bromophenols, may be formed during the reaction such that the sum of the selectivities for the p-bromophenol II and the p-benzoquinone III need not be 100%.

EXAMPLES

The following examples are set forth t o provide those of ordinary skill in the art with a detailed description of how the methods claimed herein are carried out and evaluated, and are not intended to limit the scope of what the inventors regard as their invention. Unless indicated otherwise, parts are by weight, temperature is in ° C.

Example 1

An amber 3 dram vial was charged with phenol (1.33 mL, 15.00 mmol), 48 percent hydrobromic acid (0.118 mL, 1.0 mmol of hydrogen bromide), cupric bromide (340 milligrams, 1.5 mmol) and acetonitrile (3.18 mL). The vial was loaded into an aluminum block, placed inside an autoclave and pressurized with air (1000 psi). Upon heating at 65° C. for 2 hours the autoclave was allowed to cool and the product mixture was analyzed by gas chromatography. The product mixture was found to contain 4-bromophenol (6.50% by weight), 2-bomophenol (2.00% by weight) and p-benzoquinone (6.75% by weight). These product concentrations corresponded to 54 percent overall conversion of phenol to products with a selectivity for 4-bromophenol of 23 percent and a selectivity for p-benzoquinone of 37 percent.

Example 2

An amber 3 dram vial was charged with phenol (1.33 mL, 15.00 mmol), 48 percent hydrobromic acid (0.118 mL, 1.0 mmol of hydrogen bromide), cupric bromide (340 milligrams, 1.5 mmol) and acetonitrile (3.18 mL). The vial was loaded into an aluminum block, placed inside an autoclave and pressurized with air (500 psi). Upon heating at 65° C. for 2 hours the autoclave was allowed to cool and the product mixture was analyzed by gas chromatography. The product mixture was found to contain 4-bromophenol (6.0% by weight), 2-bomophenol (2.30% by weight) and p-benzoquinone (3.25% by weight). These product concentrations corresponded to 35 percent overall conversion of phenol to products with a selectivity for 4-bromophenol of 30 percent and a selectivity for p-benzoquinone of 26 percent.

Example 3

An amber 3 dram vial was charged with phenol (1.25 mL, 14.00 mmol), 48 percent hydrobromic acid (0.118 mL, 1.00 mmol of hydrogen bromide), cupric bromide (156 milligrams, 0.70 mmol), water (0.45 mL, 25.00 mmol) and acetonitrile (3.18 mL). The vial was loaded into an aluminum block, placed inside an autoclave and pressurized with air (1000 psi). Upon heating at 65° C. for 2 hours the autoclave was allowed to cool and the product mixture was analyzed by gas chromatography. The product mixture was found to contain 4-bromophenol (3.96% by weight), 2-bomophenol (1.25% by weight) and p-benzoquinone (5.17% by weight). These product concentrations corresponded to 39 percent overall conversion of phenol to products with a selectivity for 4-bromophenol of 20 percent and a selectivity for p-benzoquinone of 41 percent.

Example 4

An amber 3 dram vial was charged with o-cresol (1.47 mL, 14.00 mmol), 48 percent hydrobromic acid (0.118 mL, 1.0 mmol of hydrogen bromide), cupric bromide (156 milligrams, 0.7 mmol), water (0.45 mL, 25 mmol) and acetonitrile (2.91 mL). The vial was loaded into an aluminum block, placed inside an autoclave and pressurized with air (1000 psi). Upon heating at 65° C. for 2 hours the autoclave was allowed to cool and the product mixture was analyzed by gas chromatography. The product mixture was found to contain 4-bromo-2-methylphenol (5.5% by weight), methyl-1,4-benzoquinone (6.40% by weight), and 6-bromo-2-methylphenol (0.6% by weight). These product concentrations corresponded to 45 percent overall conversion of o-cresol to products with a selectivity for 4-bromo-2-methylphenol of 22 percent and a selectivity for methyl-p-benzoquinone of 40 percent.

Example 5

An amber 3 dram vial was charged with m-cresol (1.46 mL, 14.00 mmol), 48 percent hydrobromic acid (0.118 mL, 1.0 mmol of hydrogen bromide), cupric bromide (156 milligrams, 0.7 mmol), water (0.45 mL, 25 mmol) and acetonitrile (2.92 mL). The vial was loaded into an aluminum block, placed inside an autoclave and pressurized with air (1000 psi). Upon heating at 65° C. for 2 hours the autoclave was allowed to cool and the product mixture was analyzed by gas chromatography. The product mixture was found to contain 4-bromo-3-methylphenol (6.2% by weight), methyl-p-benzoquinone (15.84% by weight). These product concentrations corresponded to 67 percent overall conversion of m-cresol to products with a selectivity for 4-bromo-3-methylphenol of 17 percent and a selectivity for methyl-p-benzoquinone of 65 percent.

Comparative Example 1

To a 3-dram vial were charged 1.37 ml (15.56 mmol) of phenol, 0.112 g (0.5 mmol) of cupric bromide, 1.39 ml (12.50 mmol) of 48% hydrobromic acid and 2.20 ml of acetonitrile. The vial was sealed with a cap containing a hole to allow for air flow during the reaction and placed in an aluminum block. The block was placed in a 450-ml autoclave reactor, pressurized to 34.0 atm with air and heated at 65° C. for 1 hour. It was then cooled to room temperature and depressurized. The resulting mixture was analyzed by vapor phase chromatographic analysis and shown to contain 7.39% phenol, 28.63% 4-bromophenol, 5.59% 2-bromophenol and 0.68% 2,4-dibromophenol, corresponding to 72% phenol conversion, with 82% 4-bromophenol selectivity and a total monobromophenol selectivity of 98%.

Comparative Example 2

To a 3-dram vial were charged 1.59 ml (15.39 mmol) of o-cresol, 0.112 g (0.5 mmol) of cupric bromide, 1.48 ml (12.47 mmol) of 48% hydrobromic acid and 1.92 ml of acetonitrile. The vial was sealed and located as in Example 1, pressurized to 34.0 atm with air and heated at 65° C. for 1 hour. It was then cooled to room temperature and depressurized. The resulting mixture was analyzed by vapor phase chromatographic analysis and shown to contain 13.23% o-cresol, 27.74% 4-bromo-2-methylphenol and 0.93% 6-bromo-2-methylphenol, corresponding to 56% o-cresol conversion, with 96% 4-bromo-2-methylphenol selectivity and a total monobromophenol selectivity of 99%.

Comparative Example 3

To a 3-dram vial were charged 1.37 ml (15.56 mmol) of phenol, 0.112 g (0.5 mmol) of cupric bromide, 1.30 ml (6.85 mmol) of a 30% solution of hydrogen bromide in acetic acid and 2.31 ml of acetonitrile. The vial was sealed and located as in Example 1, pressurized to 34.0 atm with air and heated at 65° C. for 1 hour. It was then cooled to room temperature and depressurized. The resulting mixture was analyzed by vapor phase chromatographic analysis and shown to contain 14.12% phenol, 19.15% 4-bromophenol and 1.15% 2-bromophenol, corresponding to 44% phenol conversion, with 96% 4-bromophenol selectivity and a total monobromophenol selectivity of 100%.

Results from Example 1 and Comparative Examples 1–3 are gathered in Table 1 and illustrate the surprising effect of acid concentration on the level of benzoquinone produced.

TABLE 1

| Example | ArOH[a] | [HBr][b] | % Conversion | "4-bromo" selectivity | benzoquinone selectivity |
|---|---|---|---|---|---|
| Example 1 | phenol | 0.06 | 54% | 23% | 37% |
| Example 2 | phenol | 0.06 | 35% | 30% | 26% |
| Example 3* | phenol | 0.07 | 39% | 20% | 41% |
| Example 4 | o-cresol | 0.07 | 45% | 22% | 40% |
| Example 5* | m-cresol | 0.07 | 67% | 17% | 65% |
| CE-1[c] | phenol | 0.8 | 72% | 96% | 0% |
| CE-2[c] | o-cresol | 0.8 | 56% | 96% | 0% |
| CE-3[c] | phenol | 0.4 | 44% | 96% | 0% |

[a]ArOH = hydroxyaromatic compound
[b]moles HBr per mole ArOH employed
[c]Comparative Example
*Water added The invention has been described in detail with particular reference to preferred embodiments thereof, but it will be understood by those skilled in the art that variations and modifications can be effected within the spirit and scope of the invention.

What is claimed is:

1. A method of preparing a mixture of a p-bromophenol and a p-benzoquinone, said method comprising contacting in a reaction mixture a hydroxyaromatic compound with:
   (a) hydrogen bromide;
   (b) at least one source of copper selected from the group consisting of copper compounds, and elemental copper; and
   (c) oxygen gas;
said hydrogen bromide being present in an amount corresponding to less than 0.2 moles of hydrogen bromide per mole of said hydroxyaromatic compound, said contacting taking place at a temperature in a range between about 20° C. and about 250° C.

2. A method according to claim 1 wherein said hydroxyaromatic compound has structure I

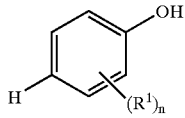

I wherein $R^1$ is independently at each occurrence a halogen, $C_1$–$C_{20}$ alkyl group, $C_4$–$C_{20}$ cycloalkyl group, or a $C_4$–$C_{20}$ aryl group, and n is an integer from 0 to 4.

3. A method according to claim 2 wherein the hydroxyaromatic compound is selected from the group consisting of phenol, and o-cresol.

4. A method according to claim 1 wherein said contacting is carried out under pressure, said pressure being in a range between about 50 psi to about 2000 psi.

5. A method according to claim 4 wherein said oxygen gas is present as a mixture with nitrogen gas.

6. A method according to claim 1 wherein said source of copper is selected from copper compounds in the group consisting of cuprous halide compounds and cupric halide compounds.

7. A method according to claim 6 wherein said copper compounds are selected from the group consisting of cuprous chloride, cuprous bromide, cuprous iodide, cupric chloride, cupric bromide, and cupric iodide.

8. A method according to claim 1 wherein said at least one source of copper is present in an amount sufficient to provide copper ion to the reaction mixture in an amount corresponding to between about 0.001 and about 0.200 moles of copper ion per mole of hydroxyaromatic compound.

9. A method according to claim 8 wherein said at least one source of copper is cupric bromide.

10. A method according to claim 8 wherein said at least one source of copper is elemental copper.

11. A method according to claim 1 wherein said reaction mixture further comprises an organic solvent, said organic solvent being selected from the group consisting of acetonitrile, propionitrile, butyronitrile, isopropylnitrile, benzonitrile, and mixtures thereof.

12. A method according to claim 11 wherein said organic solvent further comprises one or more organic solvents selected from the group consisting of, aliphatic ethers, aromatic ethers, aliphatic alcohols, aromatic alcohols, ketones, halogenated alkanes, halogenated aromatics, amides, aliphatic hydrocarbons, and aromatic hydrocarbons.

13. A method according to claim 1 further comprising a separation step, said separation step comprising transforming a mixture comprising a p-bromophenol and a p-benzoquinone into a purified p-bromophenol having a purity of at least 90 percent, and a purified p-benzoquinone having a purity of at least 90 percent.

14. A method according to claim 13 wherein said separation comprises fractional crystallization.

15. A method according to claim 13 wherein said separation comprises fractional distillation.

16. A method for the preparation of 4-bromophenol as a mixture with 1,4-benzoquinone, said method comprising contacting in a reaction mixture at a temperature in a range between about 20° C. and about 150° C., phenol with:
   (a) aqueous hydrogen bromide;
   (b) at least one source of copper selected from the group consisting of cupric bromide or cuprous bromide;
   (c) acetonitrile; and
   (d) oxygen gas;
said aqueous hydrogen bromide being present in an amount corresponding to less than 0.2 moles of hydrogen bromide per mole of phenol, said source of copper being present in an amount corresponding to between about 0.01 and about 0.20 moles of copper per mole of phenol, said acetonitrile being present in an amount corresponding to from about 0.01 to about 1.0 liters of acetonitrile per mole of phenol, said contacting being carried out under a partial pressure of oxygen of from about 50 to about 2000 psi.

17. A method according to claim 16 wherein said contacting is carried out under a partial pressure of oxygen of from about 500 to about 1000 pounds per square inch.

18. A method according to claim 16 wherein said phenol is converted to said 4-bromophenol and said 1,4-benzoquinone to the extent of at least 20 percent.

19. A method according to claim 16 wherein the selectivity for 4-bromophenol is in a range between about 20 and about 80 percent.

20. A method according to claim 16 wherein the selectivity for benzoquinone is in a range between about 80 and about 20 percent.

21. A method according to claim 16 further comprising a separation step, said separation step comprising transforming a mixture comprising a 4-bromophenol and benzoquinone into purified 4-bromophenol having a purity of at least 90 percent, and purified benzoquinone having a purity of at least 90 percent.

22. A method for the preparation of 4-bromo-2-methylphenol as a mixture with methyl-1,4-benzoquinone, said method comprising contacting in a reaction mixture at a temperature in a range between about 20° C. and about 150° C., o-cresol with:

(a) aqueous hydrogen bromide;
(b) at least one source of copper selected from the group consisting of cupric bromide or cuprous bromide;
(c) acetonitrile; and
(d) oxygen gas;

said aqueous hydrogen bromide being present in an amount corresponding to less than 0.2 moles of hydrogen bromide per mole of o-cresol, said source of copper being present in an amount corresponding to between about 0.01 and about 0.20 moles of copper per mole of o-cresol, said acetonitrile being present in an amount corresponding to from about 0.01 to about 1.0 liters of acetonitrile per mole of o-cresol, said contacting being carried out under a partial pressure of oxygen of from about 50 to about 2000 psi.

* * * * *